(12) United States Patent
Havira

(10) Patent No.: US 7,849,748 B2
(45) Date of Patent: Dec. 14, 2010

(54) METHOD OF AND AN APPARATUS FOR IN SITU ULTRASONIC RAIL INSPECTION OF A RAILROAD RAIL

(75) Inventor: Robert Mark Havira, New Fairfield, CT (US)

(73) Assignee: Sperry Rail, Inc., Danbury, CT (US)

( * ) Notice: Subject to any disclaimer, the term of this patent is extended or adjusted under 35 U.S.C. 154(b) by 195 days.

(21) Appl. No.: 12/120,759

(22) Filed: May 15, 2008

(65) Prior Publication Data

US 2009/0282923 A1 Nov. 19, 2009

(51) Int. Cl.
*G01N 29/265* (2006.01)
*G01N 29/24* (2006.01)
*G01N 29/06* (2006.01)

(52) U.S. Cl. .......................................... 73/639; 73/636
(58) Field of Classification Search ............... 73/635, 73/636, 639
See application file for complete search history.

(56) References Cited

U.S. PATENT DOCUMENTS

| | | | | |
|---|---|---|---|---|
| 3,257,843 A | * | 6/1966 | Cowan | ......................... 73/639 |
| 4,165,648 A | | 8/1979 | Pagano | |
| 4,174,636 A | * | 11/1979 | Pagano | ......................... 73/636 |
| 4,235,112 A | * | 11/1980 | Kaiser | ......................... 73/634 |
| 4,700,574 A | | 10/1987 | Turbe | |
| 5,419,196 A | * | 5/1995 | Havira et al. | .................. 73/636 |
| 5,578,758 A | | 11/1996 | Havira et al. | |
| 6,055,862 A | | 5/2000 | Martens | |
| 6,604,421 B1 | | 8/2003 | Li | |
| 2001/0032513 A1 | | 10/2001 | Havira et al. | |
| 2008/0223137 A1 | * | 9/2008 | Bestebreurtje | ............... 73/628 |
| 2009/0266166 A1 | * | 10/2009 | Pagano | ....................... 73/636 |

FOREIGN PATENT DOCUMENTS

WO WO 82/03920 * 11/1982

OTHER PUBLICATIONS

International Search Report for PCT parallel application PCT/US2009/043873.

* cited by examiner

*Primary Examiner*—Hezron Williams
*Assistant Examiner*—Rose M Miller
(74) *Attorney, Agent, or Firm*—McCormick, Paulding & Huber LLP

(57) ABSTRACT

An ultrasonic railroad rail inspection system, apparatus and method for in situ rail inspection including a wheel assembly containing a fluid-filled tire and an ultrasonic transducer mounted within the wheel assembly. The transducer is supported in the tire such that the ultrasonic beam generated by the transducer has a beam axis that intersects a head of a railroad rail at a position offset from the longitudinal median plane of the rail to the side of the head penetrated by the ultrasonic beam. The ultrasonic beam is reflected by flaws in the rail in the form of echoes. The echoes return to the transducer identifying the location of flaws.

20 Claims, 4 Drawing Sheets

METHOD OF AND AN APPARATUS FOR IN SITU ULTRASONIC RAIL INSPECTION OF A RAILROAD RAIL

FIELD OF THE INVENTION

The present invention relates, in general, to a non-destructive testing method and apparatus for certain predetermined types of undesirable flaws or defects which may be present in the rails of a railroad track. More particularly, the present invention relates to a mobile and durable type apparatus that will ultrasonically detect flaws in the rail, identify the location of the flaw when detected, and record the location of the detected flaws for possible future repair, or more likely, rail replacement. More specifically, the present invention relates to a relatively fast and sensitive method and apparatus for detecting, identifying, and recording the location of the flaws that are detected by the apparatus as the apparatus travels over the rail in situ.

BACKGROUND OF THE INVENTION

It is well recognized in the railway industry that, either through manufacturing processes or through natural environmental processes and normal use, rails of a railroad track develop certain detrimental flaws. The flaws may include both non-critical and critical defects, for example, transverse defects, vertical sheer or split head defects, and horizontal sheer or split head defects.

Safe operation on a rail may continue as long as the flaws remain non-critical. However, in time, even non-critical flaws may abscess or degrade into critical defects, and new flaws will arise. If the flaws are left unattended, the resulting defects could lead to a range of problems including catastrophic failure and train derailment. Catastrophic or even lesser failures present a financial, health and safety risk to the railway industry, transported goods and personnel, as well as surrounding homes and businesses. Such failures can be prevented, or at least decreased in frequency through routine inspection and maintenance. Further, routine maintenance can be made more cost-effective through selective repair, which is in turn facilitated by flaw detection.

To detect rail flaws or defects, ultrasonic testing has been employed. Vehicles and rail car-mounted inspection apparatus have been built to travel along the track and continuously perform ultrasonic inspection of the rails of the railroad track in situ.

In general, the inspection apparatus has taken the form of carriage-mounted sleds and wheels. A sled design, such as shown in U.S. Pat. No. 4,700,574, employs an ultrasonic transducer on a sled that is pulled along a rail coated with water to create an acoustic bridge. A wheel design, such as shown in U.S. Pat. No. 6,055,862, employs an ultrasonic transducer contained within a small, thin-walled tire that rolls along a rail. The tire is filled with fluid, such as a water-antifreeze solution, to create an ultrasonic bridge between the transducer and rail.

The prior art designs have a number of disadvantages. For example, sled designs require a large amount of water for adequate sled-to-rail coupling and reduced wear from long-distance travel. Additionally, sleds are more sensitive to imperfections and flaws on the running surface of the rail. Wheel designs suffer from acoustic reverberation (noise) caused by acoustic reflections from the surface walls of the tire. The noise reduces the sensitivity of the apparatus following each acoustic emission.

Further, both designs suffer from the limitations of known transducer technologies and configurations. Some acoustic transducer designs emit ultrasonic beams in a substantially vertical direction, which identifies some flaws in the web of the rail while lacking sensitivity to flaws in the internal portions of the head of the rail. In other designs, such as U.S. Pat. No. 4,700,574 and U.S. Pat. No. 6,055,862, transducers are positioned to emit ultrasonic beams at angles to the transverse and longitudinal planes of the rail. The axis of the beam intersects the rail at one side of the central vertical longitudinal plane of the rail and extends across the longitudinal plane of the rail to the other side. The designs identify some additional flaws in the rail, particularly in the side of the head of the rail. Still other acoustic transducer designs include more elaborate transducer assemblies with additional beam paths, but still have limited ability to identify flaws in the internal portion of the head of the rail.

SUMMARY OF THE INVENTION

The present invention, in one aspect thereof, provides a system for inspecting and detecting the location of certain types of defects in a rail of a railroad. The system includes a carriage capable of travelling on a railroad rail. A wheel assembly is suspended from the carriage and has a fluid-filled tire for rolling contact with a head of an underlying rail of the railroad rail on which the carriage travels. The tire forms a contact patch with the head of the underlying rail. An ultrasonic transducer is supported within the tire for transmitting an ultrasonic beam along a beam axis through the fluid and the tire into the head of the underlying rail. The beam axis passes into the rail at a first angle greater than 0 (zero) degrees to a vertical longitudinal median plane of the rail and a second angle greater than 0 (zero) degrees to a vertical transverse plane of the rail. The transducer is supported with the beam axis intersecting the head of the rail within the contact patch at a position offset from the vertical longitudinal median plane of the rail to the same side of the head penetrated and inspected by the ultrasonic beam.

In another aspect, the present invention provides an apparatus for inspecting and detecting the location of certain types of defects in a rail of a railroad. The apparatus includes a wheel assembly for making rolling contact with an underlying rail of a railroad rail. The wheel assembly includes a flexible tire for contact with the head of the underlying rail, the tire being filled with a fluid. At least one ultrasonic transducer is supported within the wheel assembly for transmitting an ultrasonic beam along a beam axis through the fluid and tire into the head of the underlying rail at a first angle greater than 0 (zero) degrees to a vertical longitudinal median plane of the rail and a second angle greater than 0 (zero) degrees to a vertical transverse plane of the rail. The transducer is supported within the wheel assembly to cause the beam axis to intersect the head of the rail at a position offset from the longitudinal median plane to the same side of the head penetrated and inspected by the ultrasonic beam.

In a third aspect, the present invention provides a method of ultrasonic inspection of a head of a railroad rail. The method comprises the step of directing an ultrasonic beam along a beam axis into an upper surface of the head of a rail at a first angle greater than zero (0) degrees to a vertical longitudinal median plane of the rail and a second angle greater than zero (0) degrees to a transverse-plane of the rail. The beam axis is directed to intersect the upper surface of the head of the rail at a point offset from the vertical longitudinal plane to the same side of the head of the rail penetrated and inspected by the ultrasonic beam.

In a fourth aspect, the present invention provides an apparatus for inspecting and detecting the location of certain types of defects in a rail of a railroad. The apparatus includes a wheel assembly for rolling contact with a railroad rail including an axle, a wheel hub rotatably mounted on the axle and a flexible tire mounted on the hub for rotation on the axle. The tire establishes a contact patch between a portion of the tire and a portion of the upper surface of the head of an underlying rail during an inspection. At least one ultrasonic transducer has a beam transmitting/receiving head. The transducer is mounted within the wheel assembly and is suspended from the axle with the transmitting/receiving head disposed at a predetermined distance no greater than 3 inches from the tire in the unflexed state. A fluid disposed within the wheel assembly provides the sole ultrasonic transmission medium between the transmitting/receiving head of the transducer and the portion of the tire forming a contact patch between the tire and an underlying rail.

BRIEF DESCRIPTION OF THE DRAWINGS

In the following, the invention is described in detail on the basis of preferred embodiments shown in the enclosed drawings, wherein.

DETAILED DESCRIPTION OF THE PREFERRED EMBODIMENTS

Figure 1:
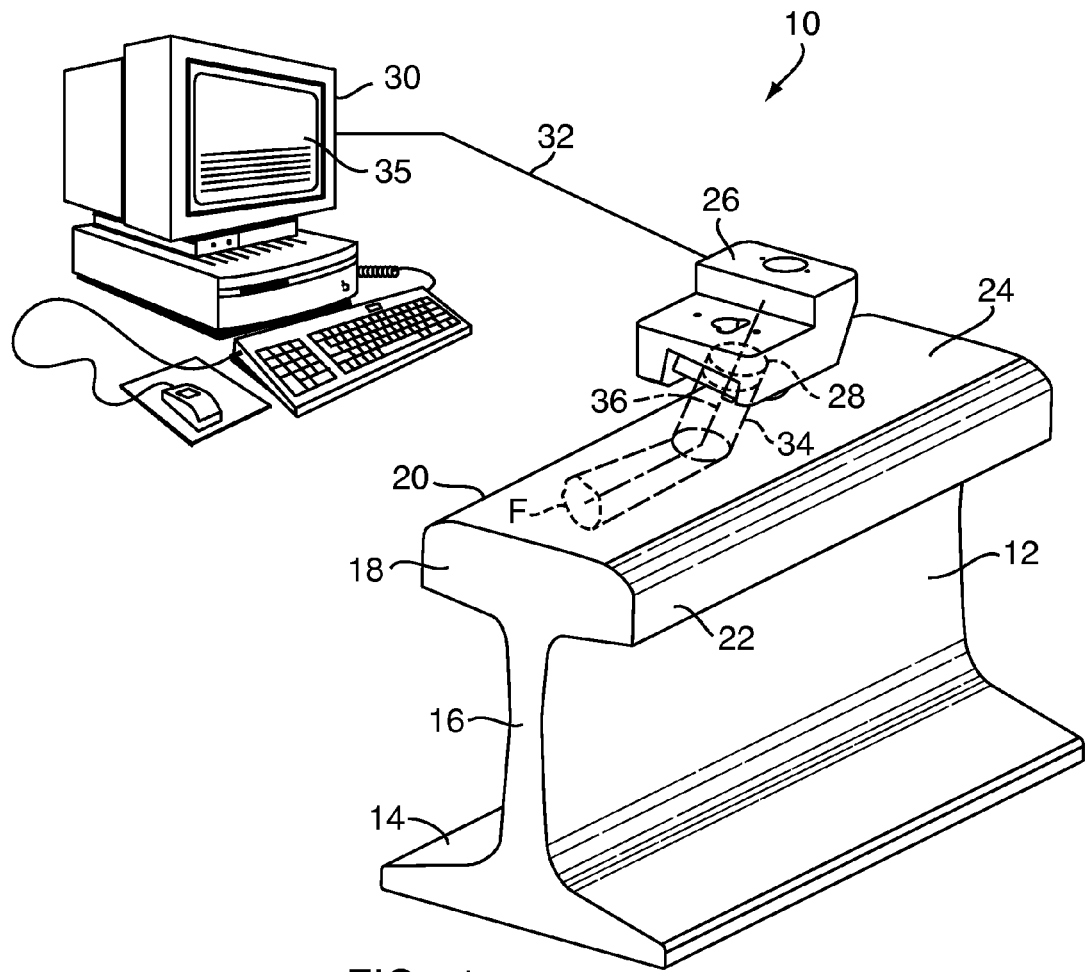
FIG. 1 is a schematic view of an ultrasonic railroad rail inspection system, illustrating a transverse defect or flaw in a railroad rail and the ultrasonic rail inspection system for detecting the flaw.

FIG. 1 shows an ultrasonic railroad rail inspection system 10 that inspects a railroad rail 12 for internal structural flaws or defects. The rail has a typical, known rail design with a base 14, a central web 16, and head 18. The head is shaped with a gauge side 20, a field side 22, and a upper running surface 24. For purposes of orientation, the directional axes of the railroad rail 12 are defined as the vertical longitudinal plane which extends vertically along the path of travel on the rail at the center or median of the rail, the horizontal longitudinal plane which extends horizontally along the path of travel on the rail, and the transverse plane which extends vertically and perpendicular to the path of travel on the rail.

The system 10 includes flaw detector or sensor 26 containing one or more ultrasonic transducers 28, which are generally transmitter-receiver transducers, that are controlled by a central processing unit 30 connected to the transducer by a cable 32 to transmit and receive ultrasonic beams. In accordance with the present invention, when the central processing unit 30 sends a signal to the transducer 28, the transducer generates and transmits an ultrasonic beam 34 along a beam axis 36 toward the head 18 of the rail such that beam axis intersects the upper surface 24 of the rail at one side of the vertical longitudinal plane of the rail. After a slight refraction, the beam propagates through the head until beam is reflected off of a flaw F embedded in the head, in the illustrated case, an oval transverse flaw located on the same side of the vertical longitudinal plane penetrated by the beam. Some of the ultrasonic beam is reflected back from the flaw along the beam axis, and propagates through the head 18 of the rail 12, through the upper surface 24 of the rail to the transducer 26 where the reflected beam is detected. The transducer converts the reflected beam into a reflection signal which the transducer sends to the central processing unit 30 through the cable 32. The central processing unit analyzes the reflection signal in comparison to the transmitted signal, and through a time scan identifies the existence, type, and location of the flaw F. The results can be stored for later analysis, or displayed in real time on the screen 35 of the central processing unit.

Figure 2:
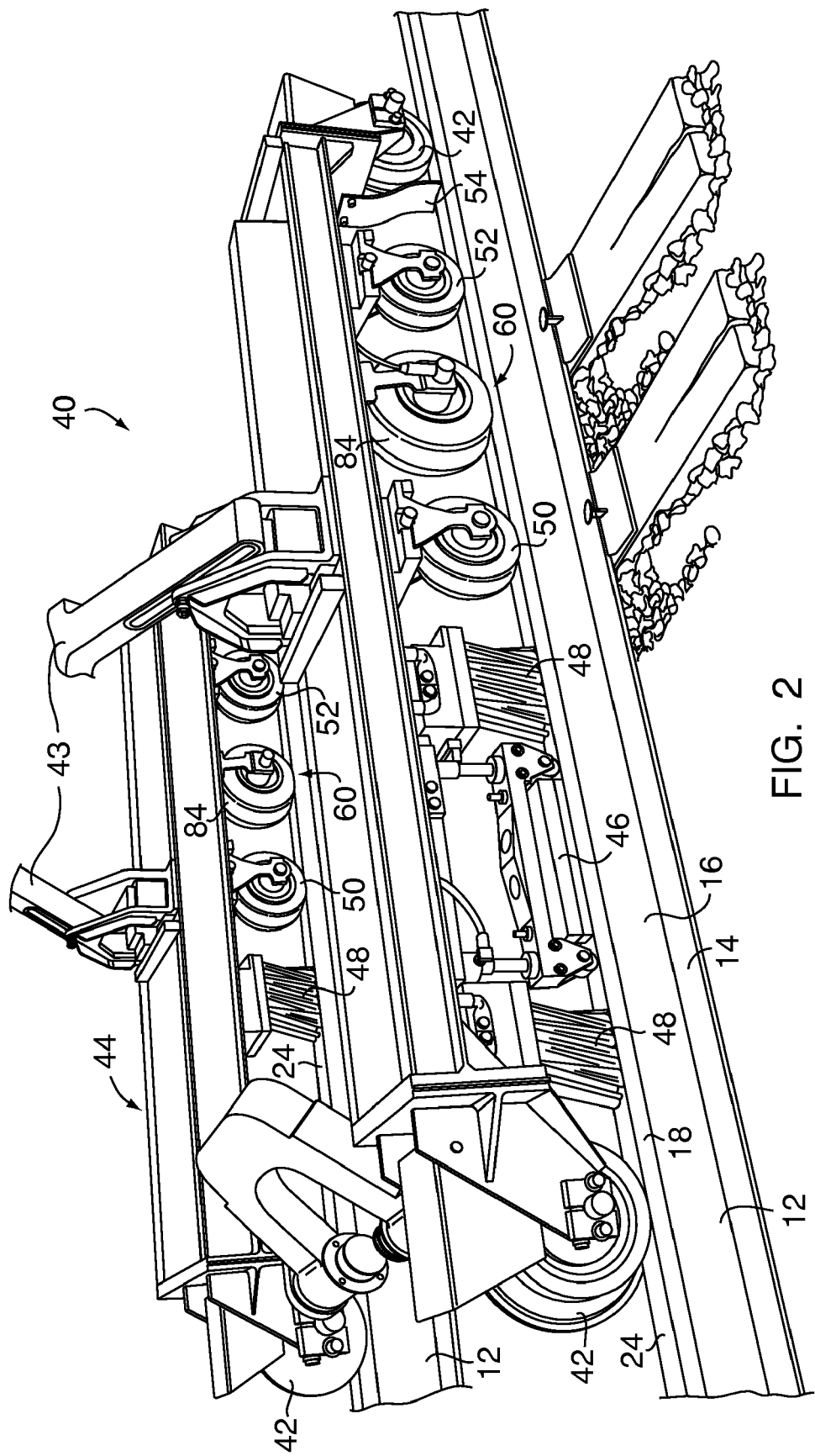
FIG. 2 is a perspective view of a carriage used in the rail inspection system of FIG. 1 for in situ ultrasonic rail inspection of a railroad rail.

Referring now to FIG. 2, a preferred embodiment of the invention utilizes a carriage 40 which in an inspection operation is suspended by links 43 under a railcar or inspection vehicle (not shown) which travels along the rails for in situ rail flaw detection and identification. The carriage 40 includes a set of four flanged carriage wheels 42 connected to the four corners respectively of a rectangular chassis 44 to guide the carriage along the rails in a substantially centered position when the carriage is lowered onto the rails in an inspection operation.

The carriage 40 may be equipped with a number of known railroad rail inspection devices and inspection accessories that operate independently or in conjunction with the present invention. For instance, the carriage may be equipped with an induction sensor assembly 46 and associated current induction brushes 48. The carriage may also be equipped with one or more known ultrasonic rail inspection wheels 50, 52, which utilize transducers set at various angles to detect flaws ahead of and behind the wheels relative to the direction of travel, as well as defects below the carriage in the web of the rails. In addition, the carriage may also be equipped with a plurality of rail cleaners 54 to remove debris from the rails in advance of the sensors and flaw detectors.

In accordance with the present invention, the carriage 40 includes freely rotatable wheel assemblies 60 that are somewhat larger in diameter than the conventional inspection wheels 50, 52, but also for in situ rail inspection. The wheel assemblies 60 are positioned between the wheels 50 and 52, but can be positioned anywhere on the carriage so as to be lowered with the other detectors into contact with the rails 12 during an inspection operation. The two wheel assemblies 60 are of the same construction and operate the same way, but on the different rails. Hence only one of the wheel assemblies 60 is described below.

Figure 4:
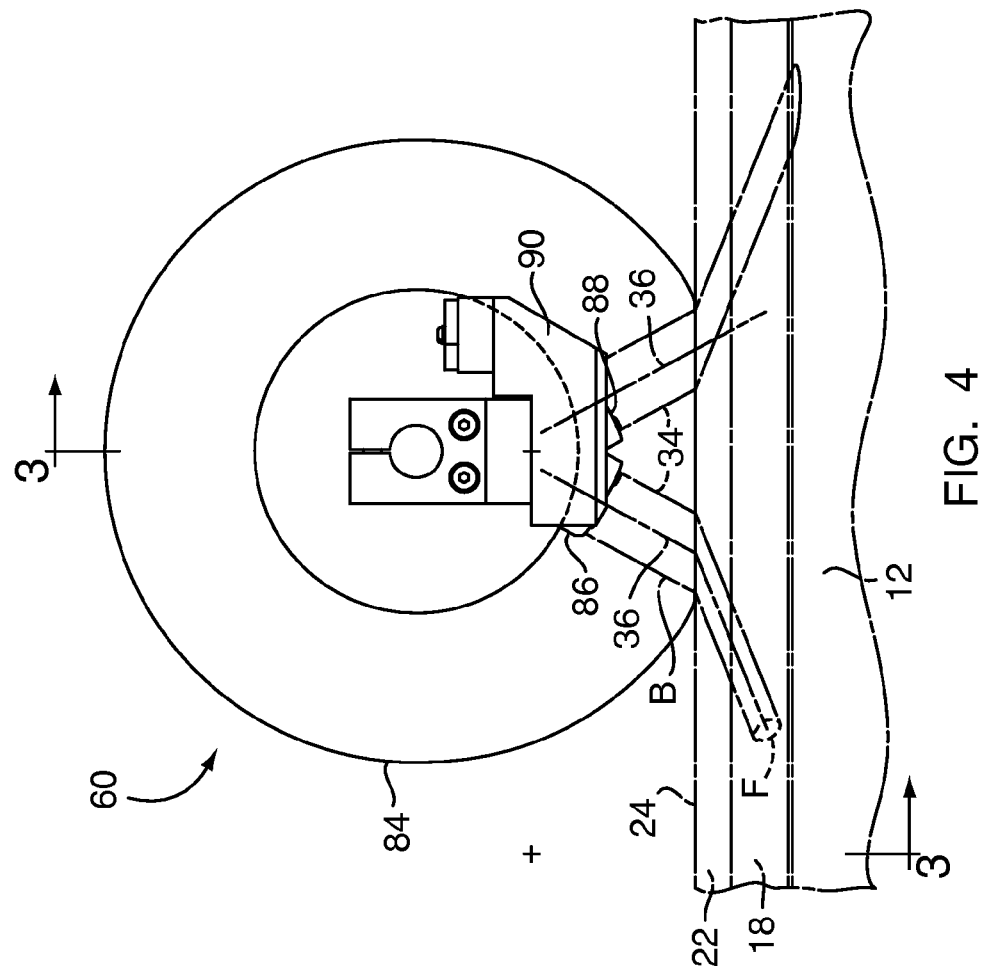
FIG. 4 is a schematic side view of a rail and the wheel assembly of the rail inspection system.
Figure 3:
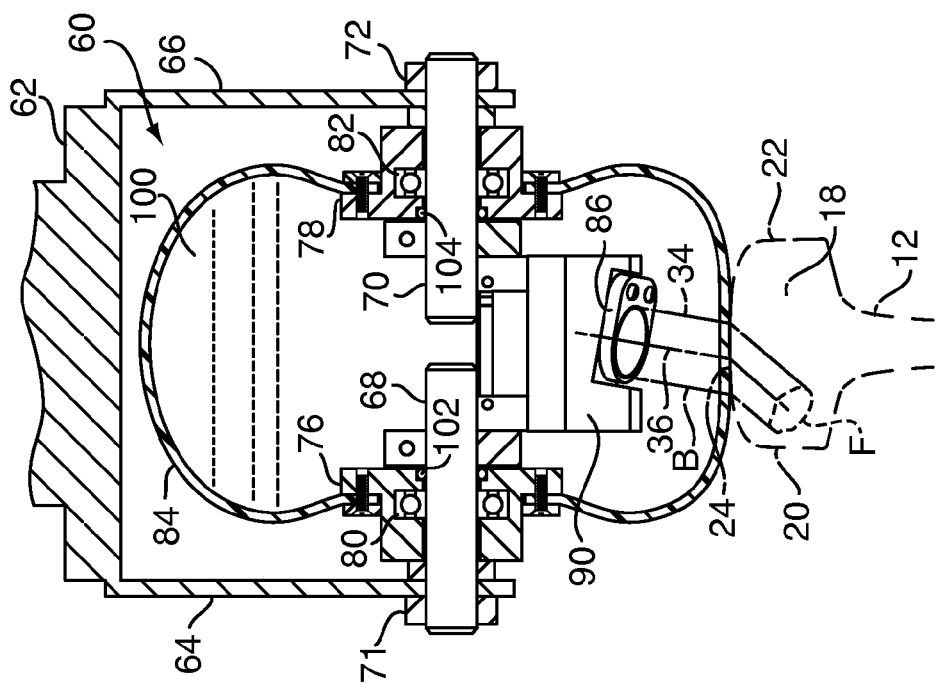
FIG. 3 is a schematic frontal view of a rail and a flaw inspection wheel assembly in cross section as viewed at the section line 3-3 of FIG. 4.

FIGS. 3 and 4 show the wheel assembly 60 in different degrees of detail. As shown in the sectional view of FIG. 3 the assembly is supported from the carriage by a bifurcated frame 62 with removable legs 64, 66 that straddle the wheel assembly. A pair of stub axles 68, 70 are releasably secured to the legs by collars 71, 72 so that the wheel assembly can be mounted in the frame 62. Once installed in the legs 64,66, the axles are fixed and secured in a non-rotatable fashion to the frame.

Figure 5:
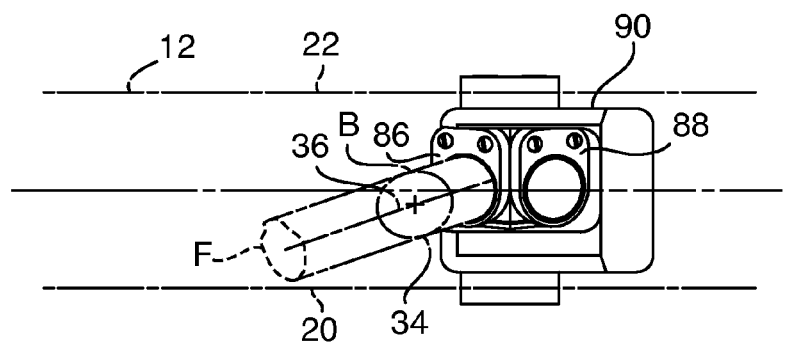
FIG. 5 is a schematic bottom plan view of a rail and the ultrasonic transducer of the wheel assembly in FIGS. 3 and 4.

As shown in FIGS. 3, 4, and 5, the wheel assembly 60 includes two hubs 76, 78 freely rotatable on the axles 68,70 by wheel bearings 80, 82 respectively, a flexible tire 84 mounted on the hubs for rotation, and a set of ultrasonic transducers 86, 88 suspended from a stationary transducer support 90 attached to the stub axles 68, 70.

The tire 84 is made of a flexible material, such as polyurethane, and is filled with a fluid 100 under a slight pressure, for example 10-15 psi. Seals 102, 104 in the hubs ride on the axles 68, 70, and prevent the fluid 100 from escaping from the tire. The fluid 100 is preferably a mixture of water and antifreeze, such as ethylene glycol, to prevent freezing.

The fluid 100 serves as an ultrasonic transmission medium, and in the illustrated embodiment is the only transmission medium between the ultrasonic transducers and the tire 84. No accessory blocks as in the prior art are needed as long as the transducers are supported in close proximity to the tire to increase the signal-to-noise ratio in the transducer signals. In the preferred embodiment, tire 84 has an outside diameter of not less than eight (8) inches, and the transducers are positioned so that the transmitting/receiving head is no more than 3 inches from the outer circumference of the tire in the unflexed state. A preferred outside diameter of the tire is about 9 inches and the transducer is preferably placed not more than 2 inches from the circumference of the tire in the unflexed state.

The tire 84 with the hubs 76,78 rotates freely on the axles 68,70 when the carriage 40 is lowered and travels along the rails 12, such that the outer circumferential surface of tire makes rolling contact with the running surface 24 of the rail head 18. As shown in FIGS. 3 and 4, the tire rests on the rail head under a slight pressure or the weight of the carriage, which causes the tire to bulge and create a contact patch with the running surface. In the preferred embodiment with an outside tire diameter of 9 inches, the contact patch with rail head 18 along the vertical longitudinal plane of the rail should be about 4 inches to assure a high transmission coupling of the ultrasonic beams between the transducers 86,88 and the rail head 18.

The ultrasonic transducers 86,88 are positioned within the tire 84 by the support 90 to project ultrasonic beams along axes into the rail head 18 at specified angles most favorable for detecting flaws in the rail head. Two transducers are used because each transducer is placed and oriented to optimally inspect half of the rail head, for example, either the gauge side or the field side of the head. The results of the inspection may be further improved by having four transducers, two facing forward and two facing backward, to detect flaws which are more likely to be exposed by beams aimed in one direction or the other. For purposes of simplicity only one forward-seeking transducer 88 and one rearward-seeking transducer 86 are shown. Additionally only the positioning and operation of the transducer 86 is discussed hereafter since the positioning and operation of the transducer 88 facing in the opposite direction are similar.

As shown in FIGS. 3, 4, and 5, the ultrasonic transducer 86 projects a beam B downward through the fluid 100 and tire 84 to intersect the upper running surface 24 of the head 18 of the underlying rail 12. In accordance with the present invention, the transducer is positioned so that the axis 36 of the beam intersects the running surface within the contact patch between the tire and rail, and at a position offset from the vertical longitudinal plane of the rail by not less than 0.2 inches to the same side of head through which the refracted beam propagates. In other words, the axis of the refracted beam does not cross over the vertical longitudinal plane as shown for example by beams 51, 52 in the prior art U.S. Pat. No. 6,055,862. After intersecting the running surface, the refracted beam passes downward into the rail head along a beam axis such that the refracted beam in the head propagates through the head at an angle of about 18±10 degrees to the vertical longitudinal plane, observable in FIG. 3, and at an angle of about 60±10 degrees to the transverse plane, observable in FIG. 4. The stated angles are preferred, and are determined by the positioning of the transducer in the wheel assembly 60. However, it has been found that penetration of the rail by the beam at a location offset to the same side of the head as inspected by the refracted beam produces significantly improved results in that more imperfections or flaws are detected than with the prior art devices.

As the beam B propagates through underlying rail head 18, the beam is reflected by deflects or flaws F, such as transverse flaws, which cause a portion of the beam to be reflected, the reflection sometimes being referred to as an echo. The echo propagates along a plurality of paths back to the running surface 24 of rail head 18, through the tire 84 and fluid 100 such that a portion of the echo reaches the transducer 86, if the transducer is an emitter/receiver transducer, or another ultrasonic detector. The received echo is converted by the transducer into a signal which is transmitted back to the processor 30 (FIG. 1) where it is analysed to determine the type and magnitude of the flaw. By pulsing the ultrasonic beam projected from the transducer 86 at a known rate, for example, 2.25 MHz, and utilizing a time scan synchronized with the carriage speed, the processor can also give the location of the flaw in the rail. All of the data can also be viewed and stored at the processor.

Figure 6:
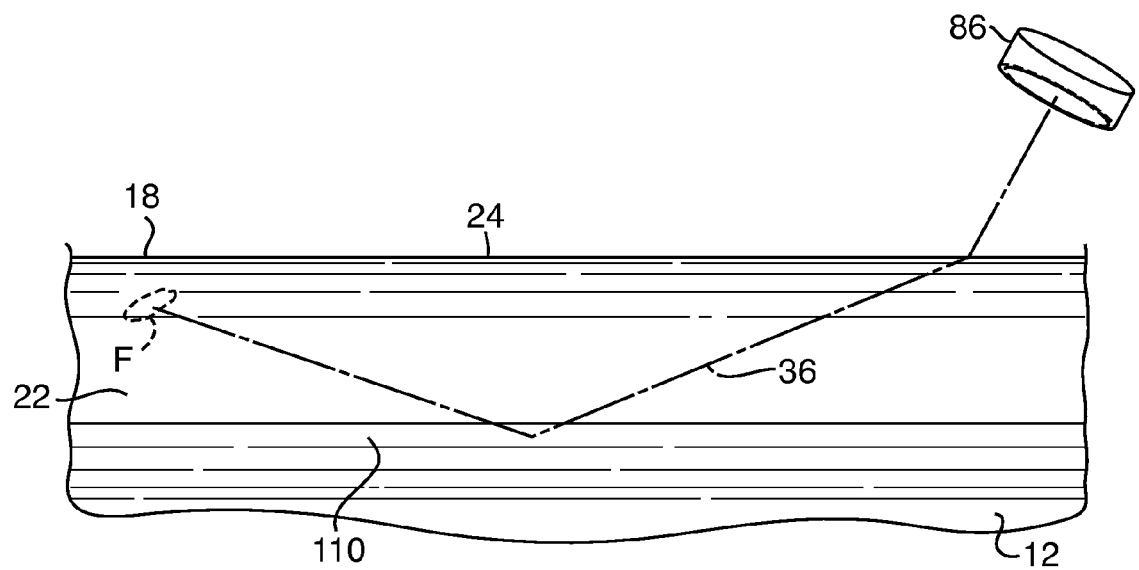
FIG. 6 is a schematic side view of a rail and the ultrasonic transducer illustrating the detection of a flaw after reflection of the ultrasonic beam in the rail head.
Figure 7:
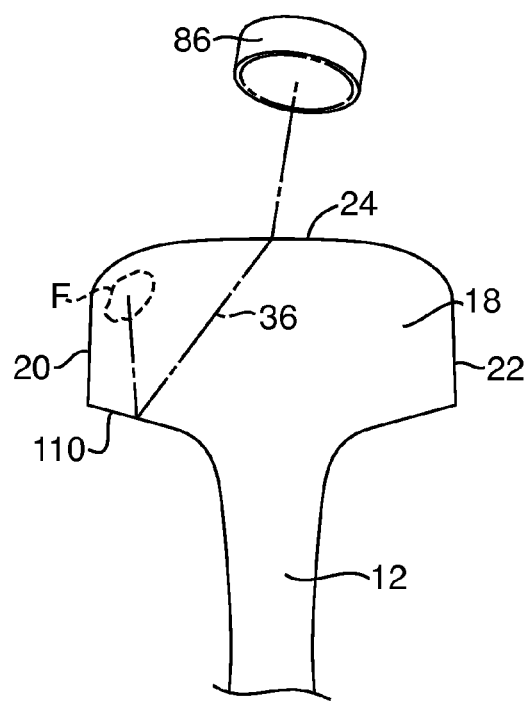
FIG. 7 is a schematic frontal view of the rail, reflected beam and transducer in FIG. 6.

As illustrated in FIGS. 6 and 7, the refracted beam with axis 36 may not encounter, or "see" a flaw F upon entry into the rail head 18 due to the orientation or position of the flaw relative to the beam, until after the beam has been reflected from the bottom side 110, gauge side 20, or field side 22 of the head. The flaw F shown is tilted at an angle which is approximately parallel to the axis 36 of the refracted beam immediately after the beam enters the rail head. Therefore, the flaw does not effectively intercept the beam at the entry angle. However, after reflection of the beam from the bottom side 110, the axis 36 of the beam is generally perpendicular to the flaw, and the flaw presents a target and discontinuity in the metal structure from which a strong beam echo will be reflected along the beam axis 36 back to the ultrasonic transducer 86 for further processing and detection. Because the beam is a pulsed beam, the processing of the reflected echo in a time scan will reveal that the flaw was detected after reflection. Therefore, flaw location can still be accurately defined.

While the present invention has been described in several embodiments, it will be understood that numerous various and substitutions can be had without departing from the spirit of the invention. For example, the wheel assembly can be utilized in combination with or independently of other flaw inspection sensors and equipment. The suspension of the transducer within the wheel assembly can take various forms as long as the position of the transducer relative to the rail can be fixed. The tire can be made of flexible materials other polyethylene as long as the ultrasonic beams can pass between the tire and the rail head. Accordingly, the invention has been disclosed in a preferred embodiment by way of illustration rather than limitation.

What is claimed is:

1. An ultrasonic railroad rail inspection system for in situ rail inspection comprising:
   a carriage capable of travelling on a railroad rail;
   a wheel assembly suspended from the carriage and having a fluid-filled tire for rolling contact with a head of an underlying rail of the railroad rail on which the carriage travels, the tire forming a contact patch with the head of the underlying rail; and
   an ultrasonic transducer being supported within the tire for propagating an ultrasonic beam along a beam axis through the fluid and the tire into the head of the underlying rail, the beam axis passing into the rail at a first angle greater than 0 (zero) degrees to a vertical longitudinal median plane of the rail and a second angle greater than 0 (zero) degrees to a vertical transverse plane of the rail, the transducer being supported such that the beam axis crosses the vertical longitudinal median plane prior to intersecting the head of the rail within the contact patch at a position offset from the vertical longitudinal median plane of the rail on the same side of the head penetrated and inspected by the ultrasonic beam.

2. The ultrasonic railroad rail inspection system for in situ rail inspection of claim 1, wherein the wheel assembly is suspended freely rotatable from the carriage.

3. The ultrasonic railroad rail inspection system for in situ rail inspection of claim 1, wherein the ultrasonic transducer is an emitter-receiver transducer.

4. The ultrasonic railroad rail inspection system for in situ rail inspection of claim 1, wherein the ultrasonic transducer is adapted to produce a pulsed ultrasonic beam and to receive a reflection of the pulsed ultrasonic beam.

5. The ultrasonic railroad rail inspection system for in situ rail inspection of claim 1, also comprising:
   another ultrasonic transducer supported within the fluid-filled tire and propagating another ultrasonic beam along a beam axis through the fluid into the underlying rail, the beam axis passing into the head of the rail at a third angle greater than zero (0) degrees to the vertical longitudinal median plane, and at a fourth angle greater than zero (0) degrees to the transverse plane, the beam axis intersecting the head on one side of the underlying rail at a position offset from the longitudinal median plane to the same side of the head penetrated and inspected by the other ultrasonic beam, but on the opposite side of the transverse plane.

6. The ultrasonic railroad rail inspection system for in situ rail inspection of claim 1, wherein the fluid-filled tire is not less than eight (8) inches in diameter.

7. The ultrasonic railroad rail inspection system for in situ rail inspection of claim 1, wherein the position offset from the longitudinal median plane is not less than 0.2 inch.

8. The ultrasonic railroad rail inspection system for in situ rail inspection of claim 1, wherein the first angle is in the range of 18±10 degrees.

9. The ultrasonic railroad rail inspection system for in situ rail inspection of claim 1, wherein the second angle is in the range of 60±10 degrees.

10. The ultrasonic railroad rail inspection system for in situ rail inspection of claim 1, wherein the transducer is supported at first angle so as to cause the ultrasonic beam in the head of the rail to be reflected off the side or bottom of the head penetrated by the ultrasonic beam.

11. An apparatus for ultrasonic in situ rail inspection, the apparatus comprising:
   a wheel assembly for making rolling contact with an underlying rail of a railroad rail, the wheel assembly including a flexible tire for contact with the head of the underlying rail, the tire being filled with a fluid; and
   at least one ultrasonic transducer being supported within the wheel assembly for propagating an ultrasonic beam along a beam axis through the fluid and the tire into the head of the underlying rail at a first angle greater than 0 (zero) degrees to a vertical longitudinal median plane of the rail and a second angle greater than 0 (zero) degrees to a vertical transverse plane of the rail, the transducer being supported within the wheel assembly to cause the beam axis to cross the vertical longitudinal median plane within the wheel assembly and to intersect the head of the rail at a position offset from the vertical longitudinal median plane to the same side of the head penetrated by the ultrasonic beam.

12. The apparatus for ultrasonic in situ rail inspection of claim 11, wherein the offset is not less than 0.2 inch.

13. A method of ultrasonic inspection of a head of a railroad rail comprising the step of:
   directing an ultrasonic beam along a beam axis into an upper surface of a head of a rail at a first angle greater than zero (0) degrees to a vertical longitudinal median plane of the rail and a second angle greater than zero (0) degrees to a transverse-plane of the rail, the beam axis being directed to cross the vertical longitudinal median plane before intersecting the upper surface of the head of the rail at a point offset from the vertical longitudinal median plane to the same side of the head of the rail penetrated by the ultrasonic beam.

14. The method of ultrasonic inspection of a head of a railroad rail of claim 13, wherein the offset is not less than 0.2 inch.

15. The method of ultrasonic inspection of a head of a railroad rail of claim 13, wherein the ultrasonic beam is a pulsed beam.

16. The method of ultrasonic inspection of a head of a railroad rail of claim 13, also comprising the step of:
   detecting an echo of an ultrasonic beam from a defect in the head of the rail.

17. An ultrasonic inspection device for detecting defects present in a head of a railroad rail, the device comprising:
   a wheel assembly for rolling contact with a railroad rail including an axle, a wheel hub rotatably mounted on the axle and a flexible tire mounted on the hub for rotation around the axle, the tire producing a contact patch between a portion of the tire and a portion of a surface of a head of the underlying rail during an inspection;
   at least one ultrasonic transducer having a beam transmitting/receiving head, the transducer being mounted within the wheel assembly and suspended from the axle with the transmitting/receiving head disposed at a predetermined distance no greater than 3 inches from the tire in the unflexed state; and
   a fluid disposed within the wheel assembly and providing the sole ultrasonic transmission medium between the transmitting/receiving head of the transducer and the portion of the tire forming a contact patch between the tire and the underlying rail,
   wherein the transmitting/receiving head defines a beam axis through the fluid and the tire into the head of the underlying rail, the beam axis passing into the underlying rail at a first angle greater than 0 (zero) degrees to a vertical transverse plane of the underlying rail, such that the beam axis crosses a vertical longitudinal median plane prior to intersecting the head of the underlying rail within the contact patch at a position offset from the vertical longitudinal median plane of the underlying rail on the same side of the head penetrated and inspected by the ultrasonic beam.

18. The ultrasonic inspection device for detecting defects as defined in claim 17 wherein the tire is not less than eight (8) inches in diameter.

19. The ultrasonic inspection device for detecting defects as defined in claim 17 wherein the fluid providing the ultrasonic transmission medium contains ethylene glycol.

20. The ultrasonic inspection device for detecting defects as defined in claim 17 wherein the predetermined distance between the transmitting/receiving head and tire in the unflexed state is not more than two (2) inches.

* * * * *